United States Patent
Hanes, Jr. et al.

(10) Patent No.: US 10,598,528 B2
(45) Date of Patent: Mar. 24, 2020

(54) MILK METER

(71) Applicant: Technologies Holdings Corp., Houston, TX (US)

(72) Inventors: Robert E. Hanes, Jr., Missouri City, TX (US); Richard L. Pettys, Jr., Pearland, TX (US); Daniel T. Nichols, Richmond, TX (US); Richard B. Voigt, Manvel, TX (US); Joel R. Henry, Manvel, TX (US); Roma M. Montifar, Houston, TX (US); David M. Headley, Manvel, TX (US); Dustin R. Reynolds, Houston, TX (US)

(73) Assignee: Technologies Holdings Corp., Houston, TX (US)

( * ) Notice: Subject to any disclaimer, the term of this patent is extended or adjusted under 35 U.S.C. 154(b) by 365 days.

(21) Appl. No.: 15/813,745

(22) Filed: Nov. 15, 2017

(65) Prior Publication Data
US 2019/0145805 A1 May 16, 2019

(51) Int. Cl.
*G01F 1/64* (2006.01)
*G01F 15/02* (2006.01)

(52) U.S. Cl.
CPC ............ *G01F 1/64* (2013.01); *G01F 15/022* (2013.01)

(58) Field of Classification Search
CPC ..... G01F 1/64; G01F 1/56; G01F 1/58; G01F 1/60; G01F 25/0007; G01F 15/075; G01F 15/022
See application file for complete search history.

(56) References Cited

U.S. PATENT DOCUMENTS

| | | | |
|---|---|---|---|
| 3,989,009 A | 11/1976 | Robar et al. |
| 5,245,946 A | 9/1993 | Hoefelmayr et al. |
| 6,604,053 B2 | 8/2003 | Fematt |
| 6,722,208 B2 | 4/2004 | Brown et al. |

(Continued)

FOREIGN PATENT DOCUMENTS

| | | |
|---|---|---|
| EP | 1443313 B1 | 3/2007 |
| JP | S5381294 A | 7/1978 |

(Continued)

OTHER PUBLICATIONS

IP Australia, Examination Report No. 1 for Standard Patent Application, Application No. 2018253618, dated Dec. 12, 2018, pp. 1-5.

(Continued)

*Primary Examiner* — Robert R Raevis
(74) *Attorney, Agent, or Firm* — Baker Botts L.L.P.

(57) ABSTRACT

An apparatus includes a tube, first and second pairs of electrodes, a reference device, and a processor. The processor determines a speed of a fluid traveling between the first and second pairs of electrodes and determines a reference conductance of the fluid using the reference device. The processor also determines a measured conductance of the fluid using at least one of the first and second pairs of electrodes and determines, based on the reference conductance and the measured conductance, a cross-sectional area of the fluid at an electrode. The processor further adds a correction factor to the determined speed to produce a bulk speed of the fluid. The processor further determines a volumetric flow rate of the fluid based on the bulk speed and the determined area and determines a volume of the fluid based on the determined volumetric flow rate.

20 Claims, 11 Drawing Sheets

(56) References Cited

U.S. PATENT DOCUMENTS

| | | |
|---|---|---|
| 6,799,474 B2 | 10/2004 | Brown et al. |
| 7,063,043 B2 | 6/2006 | Brown et al. |
| 2002/0148407 A1 | 10/2002 | Brown et al. |
| 2002/0156589 A1 | 10/2002 | Fematt |
| 2003/0130808 A1 | 7/2003 | Kapitulskiy et al. |
| 2005/0034518 A1 | 2/2005 | Wamhof et al. |
| 2015/0059491 A1 | 3/2015 | Kromwijk et al. |
| 2017/0295473 A1 | 10/2017 | Zuniga et al. |

FOREIGN PATENT DOCUMENTS

| | | |
|---|---|---|
| WO | 2007006311 A1 | 1/2007 |
| WO | 2013165236 A2 | 11/2013 |

OTHER PUBLICATIONS

European Patent Office, Extended European Search Report, Application No. 18203825.7, dated Apr. 5, 2019, 10 pages.
New Zealand Intellectual Property Office, First Examination Report, Application No. 747757, dated Jun. 4, 2019, 3 pages.
Intellectual Property Australia, Australian Examination Report No. 2 for Standard Patent Application, Application No. 2018253618, dated Mar. 21, 2019, 4 pages.

MILK METER

TECHNICAL FIELD

This disclosure relates generally to a meter for measuring a volume of fluid.

BACKGROUND

A cow can be milked by attaching a milking device to the cow's udder that automates the milking process. This automated milking process is typically faster and more efficient than milking the cow by hand. However, due to the speed at which the device milks the cow, it may be challenging to determine the volume of milk produced by the cow.

SUMMARY OF THE DISCLOSURE

This disclosure contemplates an unconventional metering device that accurately measures a volume of fluid (e.g., milk) flowing through the device in certain embodiments. The device uses electrodes and a reference device to measure the conductance of the fluid at various points in the metering device. From these conductances, the metering device determines a cross-sectional area of the fluid at an electrode. The metering device also uses the electrodes to measure a speed (e.g., surface wave speed) of the fluid as it travels through the metering device. The metering device then adds a correction factor to the measured speed to determine the bulk speed of the fluid. Then, using the bulk speed, the cross-sectional area of the fluid at an electrode, and the elapsed time, the metering device determines a total volume of the fluid. Two embodiments are described below. The first embodiment describes an apparatus (e.g., the metering device) and the second embodiment describes a method that may be performed by the metering device.

According to an embodiment, an apparatus includes a tube, a first pair of electrodes, a second pair of electrodes, a reference device, and a processor. The first pair of electrodes includes a first electrode and a second electrode coupled to the tube. The second pair of electrodes includes a third electrode and a fourth electrode coupled to the tube. The reference device is coupled to the tube. The processor determines a speed of a fluid traveling between the first pair of electrodes and the second pair of electrodes. The processor also determines a reference conductance of the fluid using the reference device and a measured conductance of the fluid using at least one of the first pair of electrodes and the second pair of electrodes. The processor further determines a conductance ratio between the measured conductance and the reference conductance, locates the conductance ratio in a lookup table, and retrieves, from the lookup table, an area corresponding to the conductance ratio. The retrieved area indicates a cross-sectional area of the fluid at one or more of the first, second, third, and fourth electrodes. The processor further adds a correction factor to the speed to produce a bulk speed of the fluid, determines a volumetric flow rate of the fluid based on the bulk speed and the determined area, and determines a volume of the fluid based on the determined volumetric flow rate.

According to another embodiment, a method includes determining a speed of a fluid traveling through a tube between a first pair of electrodes and a second pair of electrodes coupled to the tube. The first pair of electrodes includes a first electrode and a second electrode. The second pair of electrodes includes a third electrode and a fourth electrode. The method also includes determining a reference conductance of the fluid using a reference device coupled to the tube and determining a measured conductance of the fluid using at least one of the first pair of electrodes and the second pair of electrodes. The method further includes determining a conductance ratio between the measured conductance and the reference conductance, locating the conductance ratio in a lookup table, and retrieving, from the lookup table, an area corresponding to the conductance ratio. The retrieved area indicates a cross-sectional area of the fluid at one or more of the first, second, third, and fourth electrodes. The method also includes adding a correction factor to the speed to produce a bulk speed of the fluid, determining a volumetric flow rate of the fluid based on the bulk speed and the retrieved area, and determining a volume of the fluid based on the determined volumetric flow rate.

Certain embodiments provide one or more technical advantages. For example, an embodiment includes an unconventional metering device that accurately measures a volume of fluid that has flowed through the device over a period of time by measuring both a speed of the fluid flowing through the device and a conductance of the fluid. This measured volume is more accurate than measurements provided by conventional metering devices. The metering device may include particular components that further improve the accuracy of the volume measurement. For example, the metering device may include heating elements that reduce or eliminate a temperature gradient between the metering device and the fluid. By reducing this temperature gradient, the accuracy of the conductance measurement may be improved. As another example, the metering device may include one or more capacitors that remove a direct current (DC) component from electric signals traveling through the metering device. By removing the DC component from these signals, electrolysis may be prevented from occurring between the metering device and the fluid, thus improving the accuracy of the speed and conductance measurements. As another example, the metering device may include components that do not move during the operation of the metering device, which increases the lifespan of these components and reduces noise that may affect measurements. As another example, the metering device may include components that include smooth surfaces, which are easier to clean and which prevents the trapping of bacteria. Certain embodiments may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present disclosure, reference is now made to the following description, taken in conjunction with the accompanying drawings, in which.

DETAILED DESCRIPTION

Embodiments of the present disclosure and its advantages are best understood by referring to FIGS. 1 through 9 of the drawings, like numerals being used for like and corresponding parts of the various drawings.

Cows can be milked by attaching milking devices to the cows' udders that automate the milking process. Each milking device may attach to all teats of a cow's udder, which allows the cow to be milked quickly with minimal human intervention. As a result, the automated milking process is typically faster, safer, and more efficient than milking the cows by hand.

One challenge faced by automated milking processes is the ability to accurately measure the volume of milk produced by a cow. Existing milking systems use conventional metering devices that use various methods to approximate the volume of milk coming from a cow. These approximations may be helpful but may not be accurate in certain instances. This disclosure contemplates an unconventional metering device that can accurately measure the volume of milk produced by a cow. The metering device can determine this volume by first determining the speed of the milk flowing through the meter and the conductance of the milk. This metering device will be described in more detail using FIGS. 1 through 9. Although the examples in this disclosure describe the metering device in a milking environment, this disclosure contemplates the metering device being used to measure the volume of any fluid, not merely milk.

Figure 1:
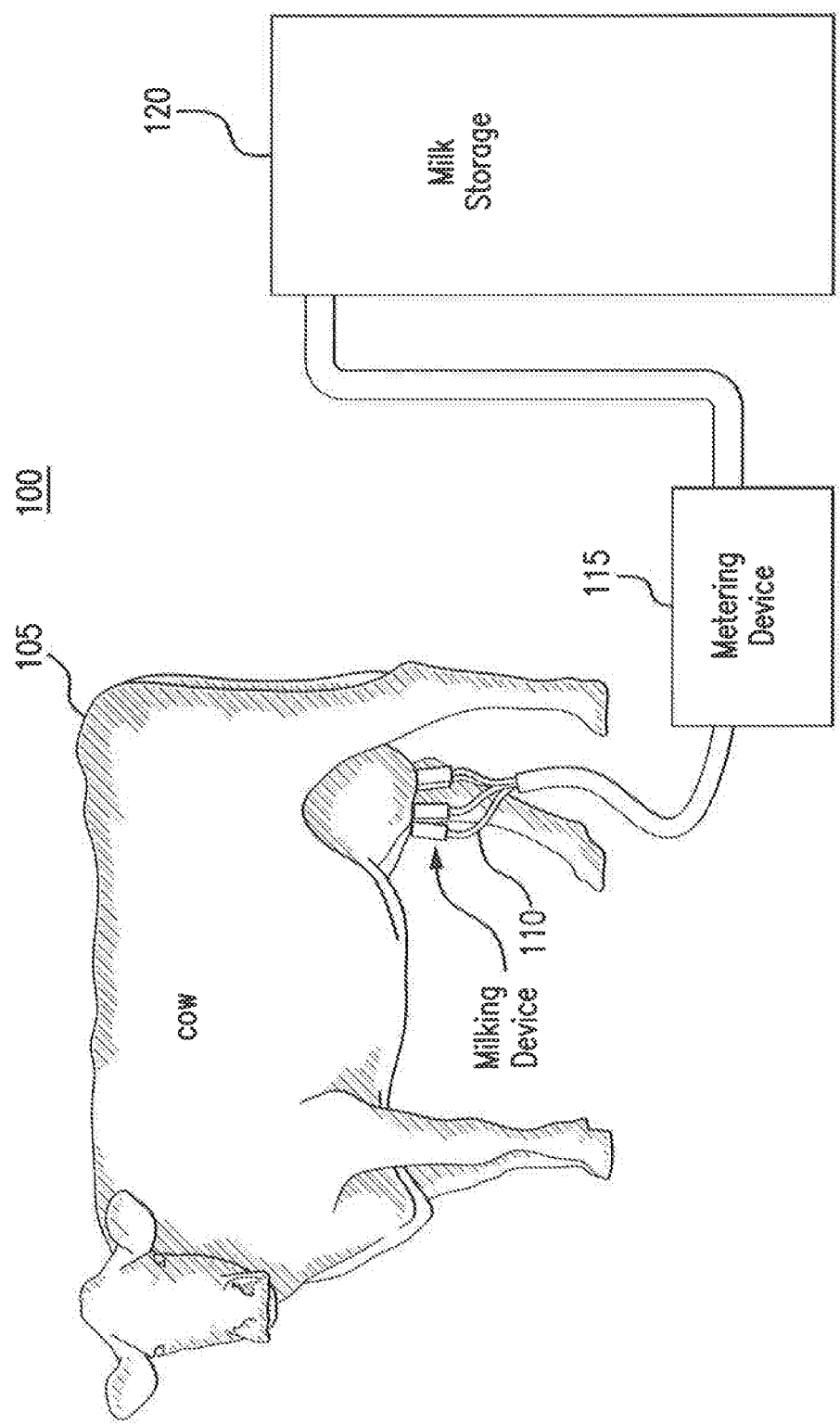
FIG. 1 illustrates an example milking system.

FIG. 1 illustrates an example milking system 100. System 100 includes a milking device 110, a metering device 115, and a storage device 120. In the example of FIG. 1, milking device 110 is attached to a cow 105. As milking device 110 milks cow 105, metering device 115 measures the volume of milk produced by cow 105. The milk is then directed to storage device 120. FIGS. 2 through 9 will describe the operation of metering device 115 in more detail.

Figure 2A:
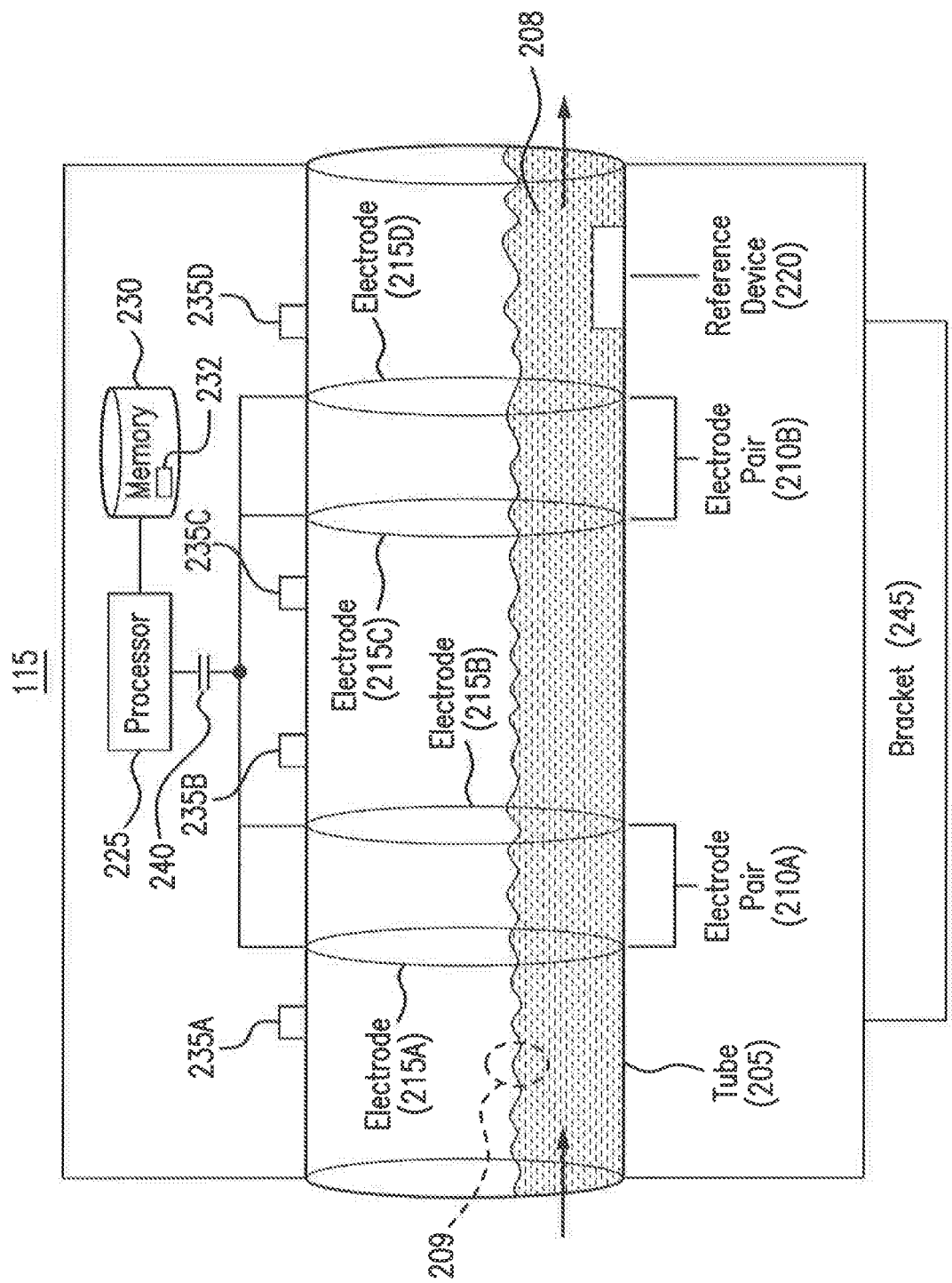
FIG. 2A illustrates an example metering device of the system of FIG. 1.

FIG. 2A illustrates the example metering device 115 of the system 100 of FIG. 1. As illustrated in FIG. 2, metering device 115 includes a tube 205. A fluid 208 (e.g., milk) flows through tube 205. Metering device 115 may measure the volume of fluid 208 that flows through tube 205 over a period of time. In certain embodiments, fluid 208 is milk but metering device 115 may be configured to measure the volume of any suitable fluid 208, such as for example, a liquid containing an electrolyte, a conductive gas, and/or a fluid with a time-varying (pulsatile or quasi-pulsatile) flow that is sufficiently large to cover the electrodes 215 and reference device 220 continuously. Metering device 115 may measure the volume of fluid 208 more accurately than conventional metering devices.

Metering device 115 includes various components that operate to measure the volume of fluid 208 flowing through tube 205. As shown in FIG. 2, metering device 115 includes a first electrode pair 210A that includes a first electrode 215A and a second electrode 215B. Metering device 115 also includes a second electrode pair 210B that includes a third electrode 215C and a fourth electrode 215D. Each electrode 215 is coupled to tube 205 and may be formed using any electrically conducting material. Each electrode 215 may be rigid, semi-rigid, or flexible. Fluid 208 flows through each electrode 215 as it flows through tube 205. The size of each electrode 215, as well as their configuration in tube 205, may be configured to optimally measure the volume of fluid 208 as disclosed later herein. Although this disclosure shows electrodes 215 being elliptical or circular in shape, this disclosure contemplates electrodes 215 (and tube 205) being of any size or shape.

In certain embodiments, components of metering device 115 are coupled to tube 205 such that these components do not move during the operation of metering device 115. For example, electrodes 215 and reference device 220 may be coupled to tube 205 such that they do not move during operation of metering device 115. Reducing the movement of these components also reduces the amount of noise in metering device 115 during operation that affect and/or degrade the accuracy of metering device 115. Thus, by preventing these components from moving, the accuracy of metering device 115 may be improved. Additionally, movement may cause components to degrade quicker over time. Thus, by preventing these components from moving, the lifespan of these components is increased.

Generally, metering device 115 determines a volume of fluid 208 that flows through tube 205 over a period of time by making several different measurements and calculations (e.g., bulk speed of fluid 208, conductance of fluid 208, cross-sectional area of fluid 208 at an electrode 215, volumetric flow rate of fluid 208). To determine this volume, metering device 115 may multiply a volumetric flow rate of fluid 208 by an elapsed time, as described later herein with respect to FIG. 5. Metering device 115 may determine the volumetric flow rate of fluid 208 by multiplying a speed of fluid 208 as it flows through tube 205 with an area (e.g., cross-sectional area) of fluid 208 at an electrode 215.

Metering device 115 may determine a cross-sectional area of fluid 208 at an electrode 215 (e.g., electrode 215A) by determining a reference conductance of fluid 208 using reference device 220 and a measured conductance of fluid 208 between two electrodes 215, as described later here in with respect to FIG. 3. Electric signals may be conducted through each electrode pair 210 and reference device 220. The electric signals may travel through one electrode 215 of the electrode pair 210, through fluid 208, and to the other electrode 215 of the electrode pair 210. Likewise, the electric signals may travel from one portion of reference device 220, through fluid 208, and to the another portion of reference device 220. The conductance of fluid 208 may affect and/or change the electric signal as it travels through fluid 208. For example, the conductance of fluid 208 may cause the electric signal to experience a voltage drop or current drop as it travels through fluid 208. Any changes to the electric signal may be sensed at electrodes 215 and at reference device 220. The reference and measured conductances of the fluid 208 may then be derived from the detected changes to the electric signal. These two conductances may differ from each other because reference device 220 may be fully submerged in fluid 208 while electrodes 215 may be partially submerged in fluid 208. Metering device 115 uses a ratio of these two conductances to determine the cross-sectional area of fluid 208 at electrode 215.

Metering device 115 may determine a surface wave speed of fluid 208 as it flows through tube 205 by dividing a distance between first and second electrode pairs 210 (e.g., electrodes 215A and 215C) by an amount of time it takes for a particular wave 209 of fluid 208 to flow from the first electrode pair 210A to the second electrode pair 210B, as described later herein with respect to FIG. 4. Metering device 115 may track wave 209 using signal analysis as it flows through tube 205 to determine the amount of time it takes for wave 209 to flow from one electrode pair 210 to another. Metering device may then determine the bulk speed of fluid 208 by adding a correction factor to the determined wave speed.

Metering device 115 includes a processor 225 and a memory 230. Processor 225 and memory 230 may be configured to perform any operation, including the measuring and detection operations, of metering device 115 described herein. For example, processor 225 and memory 230 may be configured to detect the bulk speed, conductance, and/or volume of fluid 208 flowing through tube 205.

Processor 225 is any electronic circuitry, including, but not limited to microprocessors, application specific integrated circuits (ASIC), application specific instruction set processor (ASIP), and/or state machines, that communicatively couples to memory 230 and controls the operation of metering device 115. Processor 225 may be 8-bit, 16-bit, 32-bit, 64-bit or of any other suitable architecture. Processor 225 may include an arithmetic logic unit (ALU) for performing arithmetic and logic operations, processor registers that supply operands to the ALU and store the results of ALU operations, and a control unit that fetches instructions from memory and executes them by directing the coordinated operations of the ALU, registers and other components. Processor 225 may include other hardware and software that operates to control and process information. Processor 225 executes software stored on memory to perform any of the functions described herein. Processor 225 controls the operation and administration of metering device 115 by processing information received from various components of metering device 115. Processor 225 may be a programmable logic device, a microcontroller, a microprocessor, any suitable processing device, or any suitable combination of the preceding. Processor 225 is not limited to a single processing device and may encompass multiple processing devices.

Memory 230 may store, either permanently or temporarily, data, operational software 232, or other information for processor 225. Memory 230 may include any one or a combination of volatile or non-volatile local or remote devices suitable for storing information. For example, memory 230 may include random access memory (RAM), read only memory (ROM), magnetic storage devices, optical storage devices, or any other suitable information storage device or a combination of these devices. The software 232 represents any suitable set of instructions, logic, or code embodied in a computer-readable storage medium. For example, the software 232 may be embodied in memory 230, a disk, a CI), or a flash drive. In particular embodiments, the software 232 may include an application executable by processor 225 to perform one or more of the functions of metering device 115 described herein.

Metering device 115 includes a reference device 220. In some embodiments, reference device 220 is coupled to tube 205. Reference device 220 may include two or more conducting plates and/or structures that define a channel. Fluid 208 may flow through this channel while being fully in contact with the surface area of the one or more conducting plates and/or structures. In particular embodiments, reference device 220 may be fully submerged in fluid 208 as fluid 208 flows through tube 205. As a result, reference device 220 is in complete contact with fluid 208 as opposed to electrodes 215 that may be only partially in contact with fluid 208. Reference device 220 may be used to help determine a conductance of fluid 208 as it flows through tube 205.

Figure 2B:
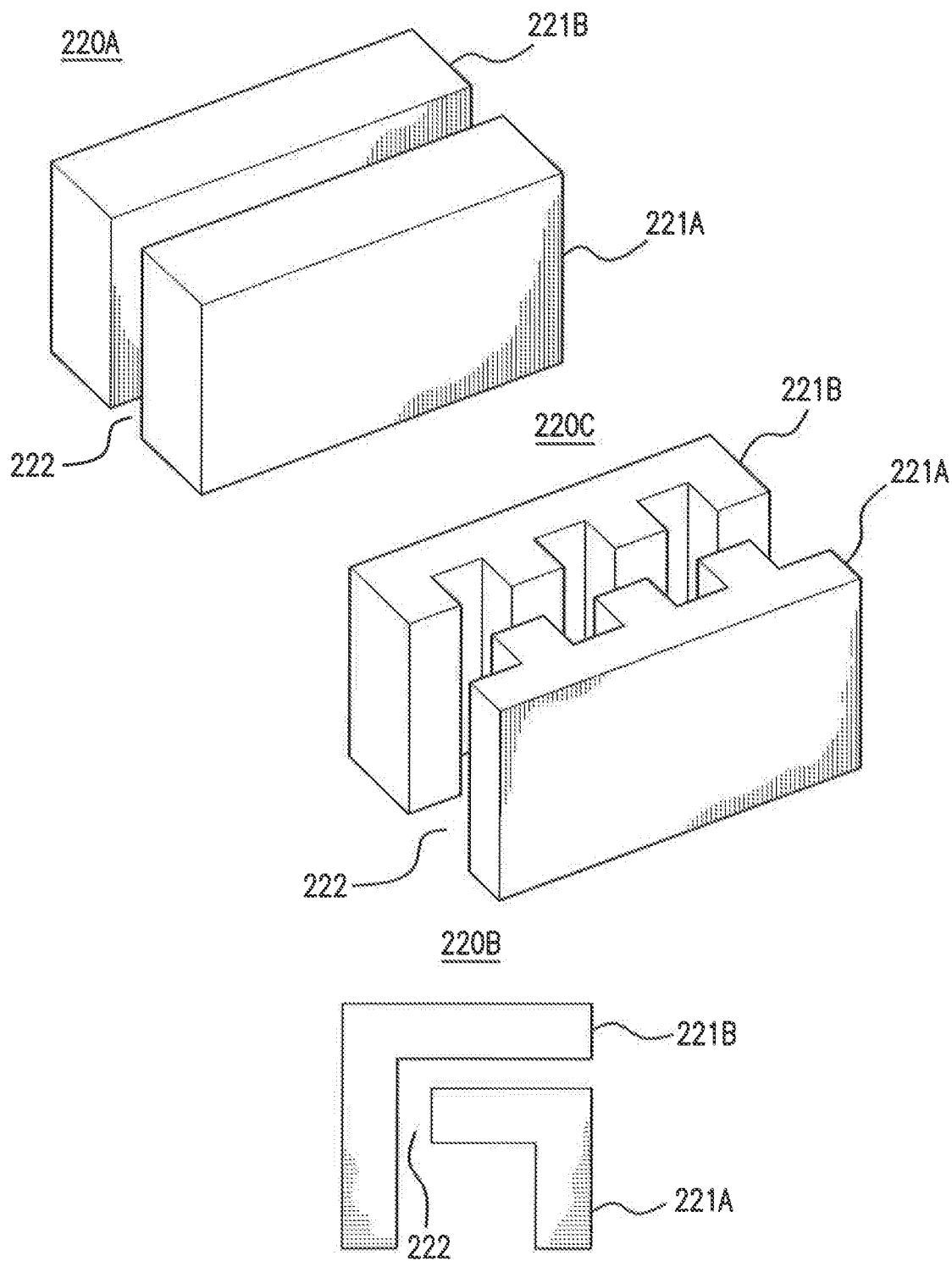
FIG. 2B illustrates example reference devices of a metering device of the system of FIG. 1.

FIG. 2B illustrates example reference devices 220 of a metering device 115 of the system 100 of FIG. 1. Four exemplary designs for reference device 220 are shown in FIG. 2B. Some designs include a first conducting structure 221A and a second conducting structure 221B. These conducting structures 221 define a channel 222 through which fluid 208 can flow. Each conducting structure 221 can be made of any suitable conducting material, such as metal for example.

Reference device 220A includes conducting structures 221A and 221B that are configured as parallel plates. Channel 222 is formed between the two parallel plates. Reference device 220B includes conducting structures 221A and 221B that are configured as overlapping plates. Channel 222 is formed between the two overlapping plates. Reference device 220C includes conducting structures 221A and 221B that are configured as interlocking plates. Channel 222 is formed between the two interlocking plates. This disclosure contemplates any suitable design for reference device 220. The illustrated designs in FIG. 2B are merely exemplary and are not intended to limit the design of reference device 220. For example, reference device 220 can be of any suitable shape. Channel 222 may be any regular path that has a well-defined geometry. In some embodiments, the shape of reference device 220A allows for easier cleaning than other reference devices 220 because channel 222 in reference device 220A is a straight channel with no bends or folds in the flow path of fluid 208. Reference device 220A may be cleaned by the force of pressurized fluid (e.g., a disinfectant solution) straight through channel 222 of reference device 220A. The pressurized fluid may be at a temperature from 100 degrees Fahrenheit to 180 degrees Fahrenheit and may be pressurized using any suitable pressure (e.g., vacuum pressure).

Metering device 115 may include additional components that improve the accuracy of the volume measurement made by metering device 115. For example, metering device 115 may include heating elements 235 coupled to tube 205 and/or electrodes 215. Each heating element 235 may heat an electrode 215 to a particular temperature, such as the temperature of fluid 208. For example, if fluid 208 is fresh milk that has been extracted from a cow, each heating element 235 may heat an electrode 215 to substantially (e.g., within five degrees Fahrenheit) 85 degrees Fahrenheit. In particular embodiments, heating electrodes 215 may remove and/or minimize a temperature gradient between electrodes 215 and fluid 208. When the temperature gradient between the fluid 208 and the electrodes 215 is large, the electrodes 215 may alter the temperature of the fluid 208 as it flows through tube 205. The temperature change may cause the conductance of the fluid 208 to change, thereby hindering the accuracy of the volume measurement made by metering device 115. By minimizing these temperature gradients, the conductance measurements, and thus the volume measurements, of fluid 208 may be more accurate.

It is understood that conductance of fluid 208 can be measured at any temperature and any temperature gradient, however the relationship between conductance ratio and cross-sectional area degrades (or degrades further) when the temperature gradient between the two conductance measurement sites (e.g., at reference device 220 and at an electrode pair 210) increases. The temperature gradient between electrodes 215 and reference device 220 may also be large, especially because electrodes 215 and reference device 220 may not absorb heat (e.g., from fluid 208) at the same rate. When electrodes 215 and reference device 220 are at different temperatures, their respective conductance measurements may be affected. As a result, the overall accuracy of metering device 115 degrades because the conductance ratios and determined cross-sectional areas may be incorrect. Heating elements 235 can ensure that electrodes 215 and reference 220 are maintained at similar temperatures in certain embodiments, thus minimizing the temperature gradient between two conductance measurement sites.

In particular embodiments, metering device 115 includes one or more capacitors 240 coupled to the electrodes 215. The one or more capacitors 240 function to remove a direct current (DC) component from the electric signals conducted to the electrodes 215. When the DC component is removed from the electric signals conducted through electrodes 215, the electrodes 215 are less likely to cause electrolysis between the fluid 208 and the electrodes 215. Electrolysis may cause fluid 208 to decompose and/or break down and attach to electrodes 215. As a result of electrolysis, electrodes 215 may become coated with various components of fluid 208 that reduce their capability to accurately measure speed and/or conductance of fluid 208. Thus, by removing the DC components using one or more capacitors 240, the accuracy of metering device 115 may be improved.

The speed at which fluid 208 flows through metering device 115 may be affected by the viscosity of fluid 208. If fluid 208 flows too quickly or too slowly through metering device 115, then the accuracy of the volume measurement may degrade. In some embodiments, metering device 115 includes a bracket 245. Bracket 245 may be used to mount metering device 115 at a particular angle. The angle may be adjustable. In some embodiments, by angling metering device 115, the flow rate and/or speed of fluid 208 may be increased and/or decreased. For example, the speed of fluid 208 is increased by increasing the angle at which metering device 115 is mounted and the speed of fluid 208 is decreased by decreasing the angle at which metering device 115 is mounted. The accuracy of metering device 115 may be improved in certain embodiments by adjusting the speed of fluid 208 flowing through tube 205 by adjusting the angle at which metering device 115 is mounted.

In certain embodiments, metering device 115 includes a switching regulator. The switching regulator operates to reduce the electric noise in metering device 115, which may improve the accuracy of the measurements made by metering device 115.

In some embodiments, certain components of metering device 115 (e.g., electrodes 215 and reference device 220) may be electrically isolated. For example, these components may be coupled to a different ground than earth ground. As a result, these components may see less electrical noise and feedback, which improves their accuracy in measuring the volume of fluid 208.

The process by which metering device 115 determines the volume of fluid 208 flowing through tube 205 will be described in more detail using FIGS. 3 through 5.

Figure 3:
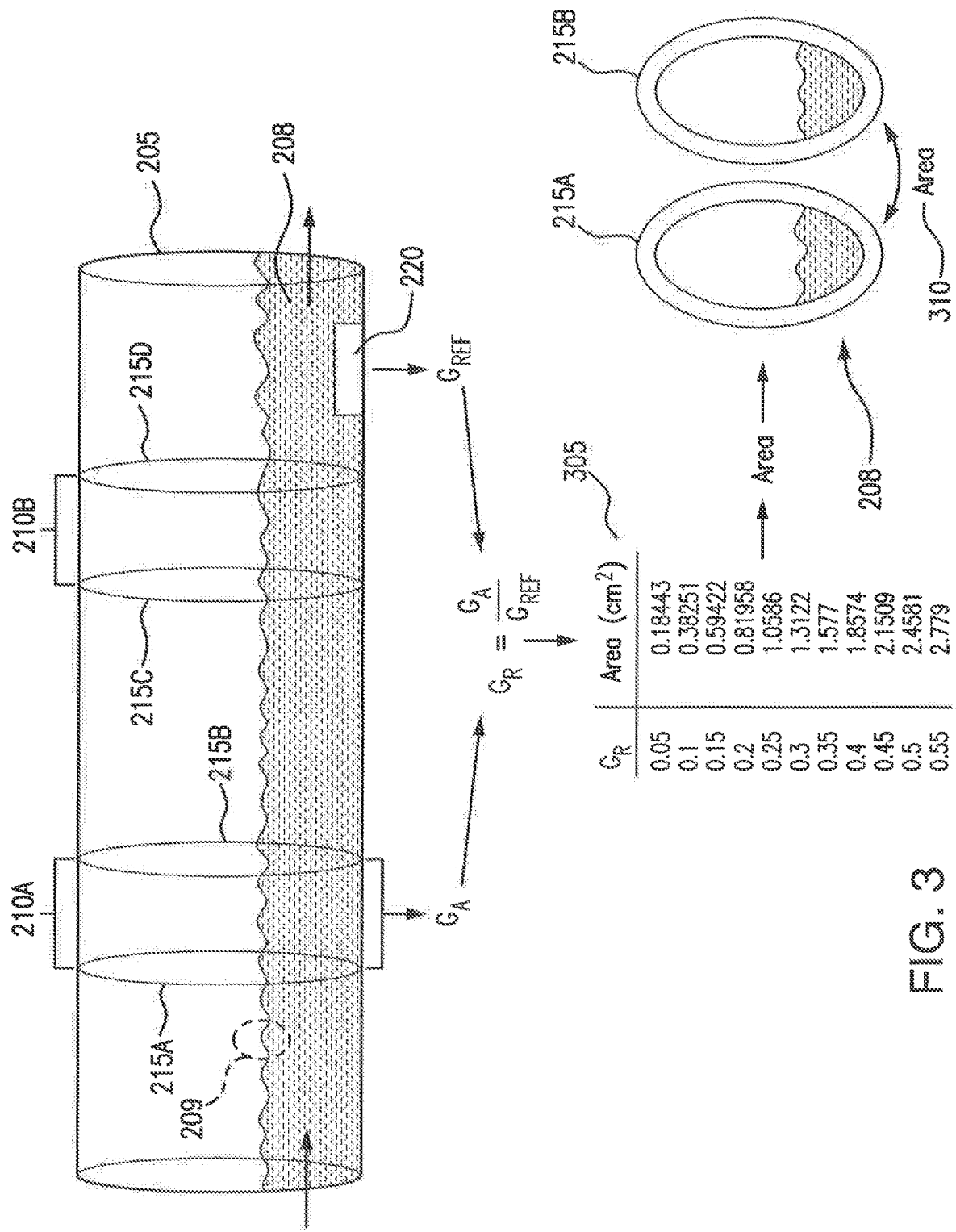
FIG. 3 illustrates the example metering device of the system of FIG. 1 determining a cross-sectional area of a fluid at an electrode.

FIG. 3 illustrates the example metering device 115 of system 100 of FIG. 1 determining a cross-sectional area of fluid 208 at an electrode 215. For clarity, not all components of metering device have been illustrated. Generally, metering device 115 determines a cross-sectional area 310 of fluid 208 at an electrode 215 by measuring the conductance of the fluid 208. Cross-sectional area 310 may occupy a plane that is substantially orthogonal to the flow of fluid 208 in tube 205 and substantially parallel to the planes of one or more electrodes 215. The greater the volume of fluid 208 in tube 205, the greater the cross-sectional area 310.

Metering device 115 determines two conductances that it uses to determine the cross-sectional area 310 of fluid 208 at electrode 215. As shown in FIG. 3, metering device 115 first determines a conductance of fluid 208 using electrodes 215, such as electrodes 215A and 215B. This disclosure contemplates that metering device 115 may also determine a conductance of fluid 208 using electrodes 215C and 215D. This determined conductance is labeled $G_A$. Metering device 115 may determine this conductance by conducting an electric signal from electrode 215A, through fluid 208, to electrode 215B. First, metering device 115 conducts an electric signal (e.g., using a signal generator) from electrode 215A through fluid 208 to electrode 215B. The conductance of fluid 208 may cause the electric signal to experience a change (e.g., voltage drop, current drop, etc.) as it travels through fluid 208. Metering device 115 can compare the electric signal received at electrode 215B with the electric signal conducted through electrode 215A to determine this change. Then, metering device 115 can determine the conductance of fluid 208 according to Ohm's Law (Conductance is equal to Current divided by Voltage) by, for example, dividing the electric current of the electric signal by a measured voltage drop.

The volume of fluid 208 in tube 205 will affect the conductance measured by metering device 115. As the volume of fluid 208 increases, so does the cross-sectional area 310 of fluid at electrodes 215A and 215B. As this cross-sectional area 310 increases, according to Pouillet's Law (Conductance is directly proportional to Area divided by Length), so does the measured conductance and the amount of electric current conducted through fluid 208 between electrodes 215A and 215B. Although the conductivity of fluid 208 (e.g., the conductance measured by conducting an electric signal through reference device 220) does not change, the measured conductance will change because the amount of cross-sectional area 310 of fluid 208 changes. Thus, there exists a correlation between the volume of fluid 208 in tube 205 and/or cross-sectional area of fluid 208 at an electrode 215 and the measured conductance of that fluid 208.

To determine the cross-sectional area 310 of fluid 208 at electrode 215, metering device 115 then determines a reference conductance of fluid 208 (e.g., the measured conductance of fluid 208 if all of the surface area of electrodes 215A and 215B were in contact with fluid 208). Metering device 115 may use reference device 220 to determine this reference conductance. Similar to measuring conductance using electrodes 215A and 215B, metering device 115 may conduct an electric signal (e.g., by a signal generator) through fluid 208 between two portions (e.g., metal plates or two different portions of a single metal structure/plate) of reference device 220 and may measure changes (e.g., voltage drop, current drop, etc.) experienced in the electric signal between the two conducting structures. Contrary to electrodes 215A and 215B, however, reference device 220 is fully submerged in fluid 208 as discussed above. Thus, all of the surface area of reference device 220 may be in contact with fluid 208. As a result, the conductance and/or conductivity of fluid 208 measured using reference device 220 may fully determine the reference conductance of fluid 208. This measured conductance is labeled $G_{REF}$.

This disclosure contemplates metering device 115 determining conductance of fluid 208 using any suitable process or circuit. For example, metering device 115 may conduct a constant voltage electric signal and measure any experienced current drop in the electric signal as it travels through fluid 208. As another example, metering device 115 may conduct a constant current electric signal and measure any experienced voltage drop in the electric signal as it travels through fluid 208. As yet another example, metering device 115 may use a current divider circuit to determine a current and/or voltage drop in the electric signal as it travels through fluid 208.

Metering device 115 may calculate a conductance ratio ($G_R$) by dividing $G_A$ by $G_{REF}$. This conductance ratio may then be used to index a lookup table 305 that correlates various conductance ratios with cross-sectional areas. Lookup table 305 may include a plurality of entries. Each entry may indicate a particular conductance ratio and a cross-sectional area corresponding to that conductance ratio. Based on the lookup table 305, metering device 115 may determine the cross-sectional area of fluid 208 at an electrode 215. Using the example of FIG. 3, if metering device 115 measures a conductance ratio of 0.05, then metering device 115 may determine based on lookup table 305 that the cross-sectional area is 0.18443 cm$^2$. As another example, if metering device 115 measures a conductance ratio of 0.1, then metering device 115 may determine based on lookup table 305 that the cross-sectional area is 0.38251 cm$^2$. It is understood that these conductance ratios and areas are merely exemplary. This disclosure contemplates the lookup table 305 including any suitable values. For example, the conductance ratios may be any value from zero through one, but may be greater than one, and the cross-sectional areas may be any suitable cross-sectional areas of fluid 208.

For example, metering device 115 may use electrodes 215 to measure a conductance ($G_A$) of fluid 208 to be 4 milliSiemens (mS). Metering device 115 may use reference device 220 to measure a reference conductance ($G_{REF}$) of fluid 208 to be 16 mS. Metering device 115 may then divide the measured conductance by the reference conductance to produce a conductance ratio ($G_R$) of 0.25. Lookup table 305 may include an entry indicating that a cross-sectional area corresponding to a conductance ratio of 0.25 is 1.0586 cm$^2$. Metering device 115 may locate the entry in the lookup table 305 that includes the entry with the conductance ratio and retrieve the cross-sectional area in that entry. In some embodiments, lookup table 305 may not include an entry that includes the conductance ratio calculated by metering device 115. In these instances, metering device 115 may select an entry in lookup table 305 that includes a conductance ratio that is closest to the conductance ratio determined by metering device 115 (also referred to as nearest-neighbor interpolation). In some instances, metering device 115 may truncate or round the conductance ratio determined by metering device 115 until it matches the conductance ratio of an entry in lookup table 305. In some embodiments, interpolation (e.g., nearest-neighbor lookup or linear interpolation) based on lookup table 305 may be used to determine cross-sectional areas 310 for conductance ratios that have no entry in lookup table 305.

Metering device 115 and lookup table 305 may be calibrated for any fluid 208. In particular embodiments, the lookup table 305 may be derived through experimentation and/or extrapolation. For example, a known volume of fluid 208 may be sent at a steady rate through metering device 115 with a tube 205 whose volume is also known. Because the steady rate and volumes of tube 205 and fluid 208 are known, the height of fluid 208 in tube 205 is also known. Based on that height, the cross-sectional area 310 of fluid 208 at an electrode 215 can be calculated. The conductance ratio for that volume of fluid may be measured using the process described above. The measured conductance ratio and the calculated cross-sectional area are then added as one entry in lookup table 305 This process can be performed for different volumes of fluid 208 to create additional entries into the lookup table 305.

Figure 4:
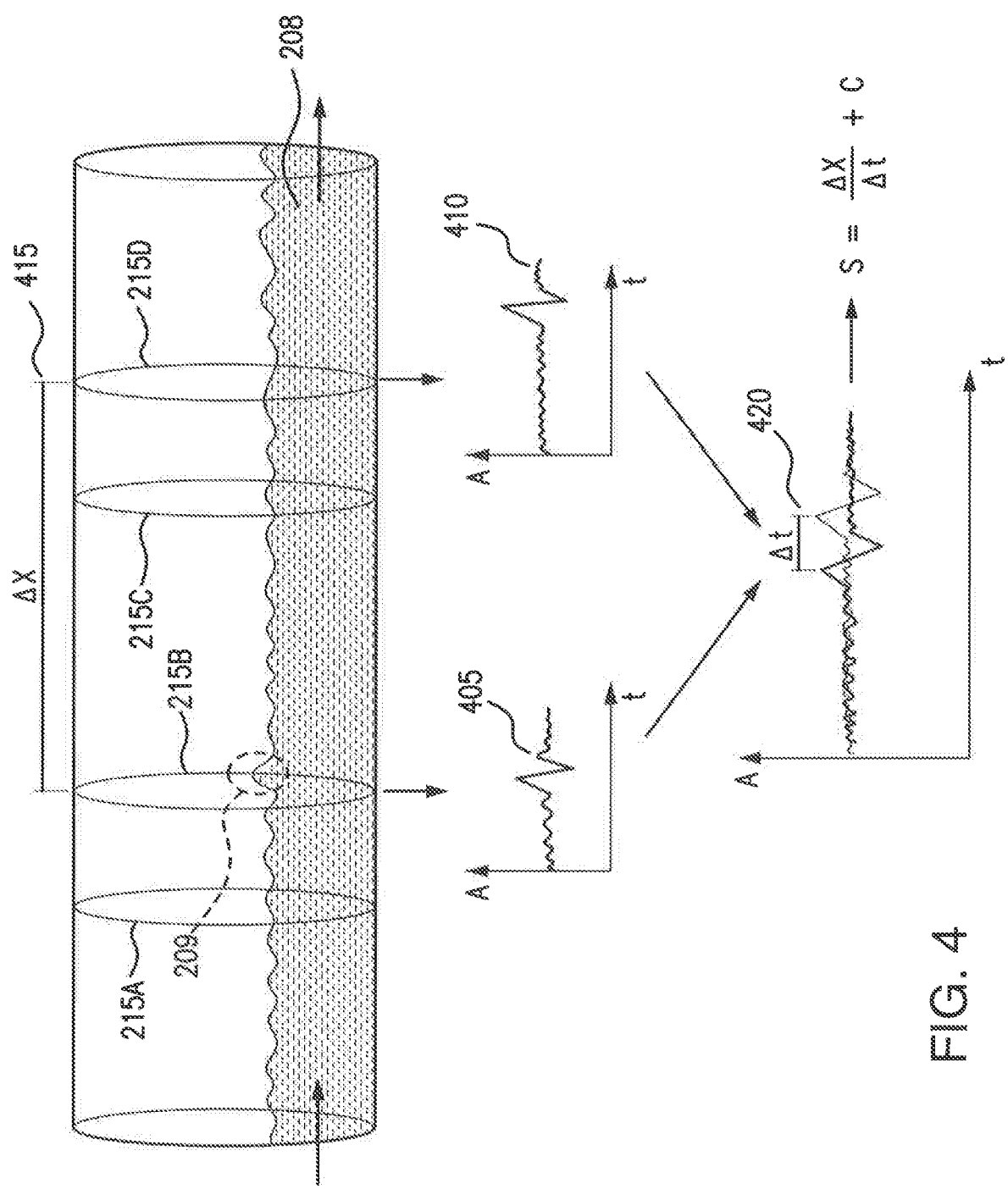
FIG. 4 illustrates the example metering device of the system of FIG. 1 determining the bulk speed of a fluid.

FIG. 4 illustrates the example metering device 115 of system 100 of FIG. 1 determining the bulk speed of a fluid 208. For clarity, certain components of metering device 115 are not illustrated in FIG. 4. Generally, to determine the speed of fluid 208, metering device 115 measures the amount of time it takes for fluid 208 to flow from one electrode 215 to another electrode 215. The speed of fluid 208 may be determined using that measured time and the known distance between the electrodes 215. As shown in FIG. 4, electrodes 215B and 215D are separated by a known distance 415. This distance 415 is labeled as ΔX. This disclosure contemplates distance 415 being any suitable value. However, certain distances 415 (e.g., distance(s) described with respect to FIG. 7) may provide optimal volume measurements.

Metering device 115 may determine how long it takes for a surface wave of fluid 208 to flow between two electrodes 215 by tracking the waves and/or wave patterns in fluid 208. As shown in FIG. 4, fluid 208 has waves and/or wave patterns that flow through electrodes 215B and 215D (or through electrode pairs 210). One wave 209 of fluid 208 will flow through electrode 215B and then at a later period in time, through electrode 215D. By tracking the wave patterns that flow through electrodes 215B and 215D, it may be possible to determine the points in time at which that wave 209 flowed through those electrodes 215.

For example, graph 405 shows the detected wave pattern flowing through electrode pair 210A over a period of time and graph 410 shows the detected wave pattern flowing through electrode pair 210B over that same period of time. As can be seen in these graphs, a wave travels through electrode 215B and then at a later time, through electrode 215D. Metering device 115 may analyze the wave patterns at various electrode pairs (e.g. electrode pair 210A and electrode pair 210B) to identify particular waves in the wave pattern and to determine when those waves have traveled to certain electrode pairs. For example, metering device 115 may, at a first electrode pair (e.g., electrode pair 210A) at a first time, determine and track identifying characteristics of a wave, such as the amplitude and frequency of the wave as well as the amplitudes and frequencies of adjacent waves. Metering device 115 may then analyze the wave pattern at a second electrode pair (e.g., electrode pair 210B) to determine when (e.g., at a second time) a wave with similar and/or substantially identical identifying characteristics is detected at that second electrode pair. Metering device 115 may identify the similar wave at the second electrode pair as the original wave identified at the first electrode pair. Metering device may then determine the amount of time it took for the wave to flow from the first electrode pair to the second electrode pair. This time difference is shown in graph 420 and is labeled Δt. The surface wave speed of fluid 208 may then be derived by dividing the distance 415 between the electrodes 215 by the measured time difference Δt. This disclosure contemplates metering device 115 analyzing any suitable characteristic of a wave or wave pattern to identify the wave.

Conventional metering devices may use the surface wave speed to calculate the volume of fluid 208. Such an approach however may result in an error in excess of 10% because the surface wave speed may not be the speed of the bulk fluid 208 flowing beneath the waves. Metering device 115 converts the determined surface wave speed to a bulk speed of fluid 208 by adding a correction factor (labeled 'C' in FIG. 4) to the determined wave speed. In FIG. 4, the bulk speed is labeled S. By using bulk speed of fluid 208 rather than surface wave speed, metering device 115 exhibits improved accuracy over conventional metering devices. It is important to recognize that some correction should be done to transform the wave speed to the bulk speed. Although this disclosure contemplates adding a correction factor (C) to produce a bulk speed, this disclosure contemplates performing any mathematical operation involving a correction factor and the wave speed to produce a bulk speed of the fluid. For example, the bulk speed may similarly be produced by subtracting, multiplying, or dividing the wave speed by a correction factor.

The correction factor may be determined empirically. For example, a pump may be used to pump fluid 208 through metering device 115 at a known volumetric flow rate. The surface wave speed of fluid 208 may be measured as described above and the cross-sectional area of fluid 208 may be determined according to the process described with respect to FIG. 3. Because the volumetric flow rate is the product of the cross-sectional area and the bulk speed (which is derived from the surface wave speed), as discussed later with respect to FIG. 5, it is possible to solve for the correction factor when the volumetric flow rate is known, as is the case with the pump. For example, correction factors for various volumetric flow rates and cross-sectional areas may be plotted and a curve may be extrapolated. In some embodiments, the correction factor may be expressed as a function (e.g., an N-th order polynomial) of the cross-sectional area of fluid 208 at an electrode 215.

In operation, metering device 115 may determine the correction factor by first determining the cross-sectional area of fluid 208 as discussed above with respect to FIG. 3. Then, metering device 115 may apply that determined cross-sectional area to the function (e.g., N-th order polynomial) to determine the correction factor. Metering device 115 may then add the correction factor to the measured wave speed to produce the bulk speed of fluid 208.

Figure 5:
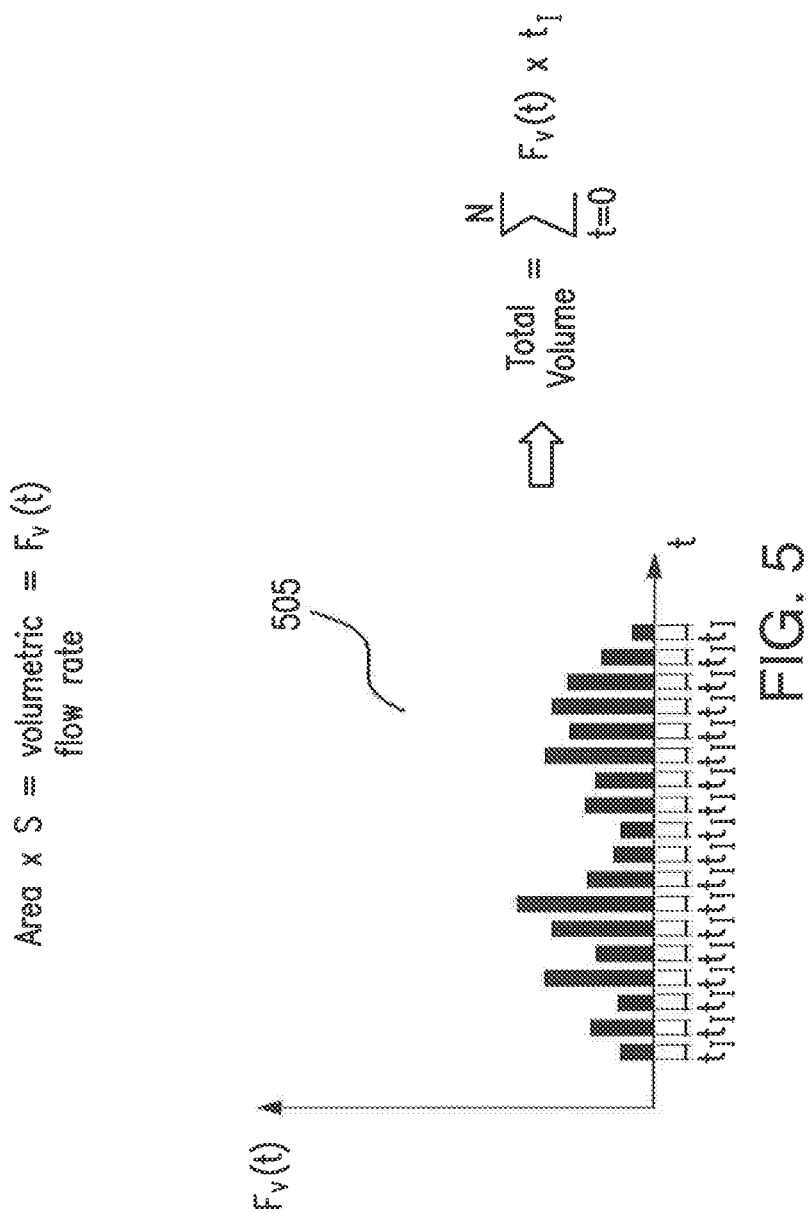
FIG. 5 illustrates the example metering device of the system of FIG. 1 determining a total volume of a fluid.

FIG. 5 illustrates the example metering device 115 of system 100 of FIG. 1 determining a total volume of a fluid. Metering device 115 determines the volume of a fluid by determining the volumetric flow rate of the fluid at points in time.

As described in FIGS. 3 and 4, metering device 115 may determine the bulk speed of the fluid and a cross-sectional area of the fluid by using lookup table 305, for example. Metering device 115 may then determine the volumetric flow rate by multiplying the cross-sectional area of the fluid (shown in FIG. 3) by the bulk speed of the fluid (shown in FIG. 4). The volumetric flow rate is labeled $F_V(t)$. The volumetric flow rate is the volume of fluid 208 flowing through the electrodes per unit time. Metering device 115 may determine the volumetric flow rate at various points in time. Each measurement may take place across a particular time interval $(t_1)$, which can be treated by metering device 115 as the unit time.

As seen in FIG. 5, metering device 115 has determined the volumetric flow rate at eighteen points in time shown in graph 505. Each volumetric flow rate measurement occurs over the unit time $(t_I)$. The time interval $(t_I)$ across which a single volumetric flow rate measurement is determined may be adjusted to improve the accuracy and/or granularity of metering device 115. Additionally, the time between measurements of volumetric flow rate can also be adjusted to improve the accuracy and/or granularity of metering device 115. Ideally, the time between measurements and the time interval $(t_I)$ for a measurement is as small as possible.

The volume of fluid 208 across a time interval $(t_I)$ of a measurement may be derived by multiplying the volumetric flow rate by the time interval $(t_I)$ (also referred to as the rectangular method). In graph 505, this volume is the area of the curve underneath one measurement of $F_V(t)$. The total volume of fluid 208 may be calculated by summing these volumes across a period of time. Using the example of FIG. 5, the total volume of fluid 208 is calculated by summing up the areas underneath the nine curves. In other words, the total volume is the sum of each measurement of $F_V(t)$ multiplied by $t_I$. As the time between measurements and the time interval $(t_I)$ for measurements are decreased, metering device 115 is effectively integrating $F_V(t)$ across a period of time to determine the total volume of fluid that flowed through metering device 115 during that period of time. It is understood that other forms of numeric integration may be performed to determine the volume of fluid 208, such as for example, trapezium method, midpoint method, Simpson's method, quadratic triangulation, Romberg method, and Gauss quadrature method.

Figure 6:
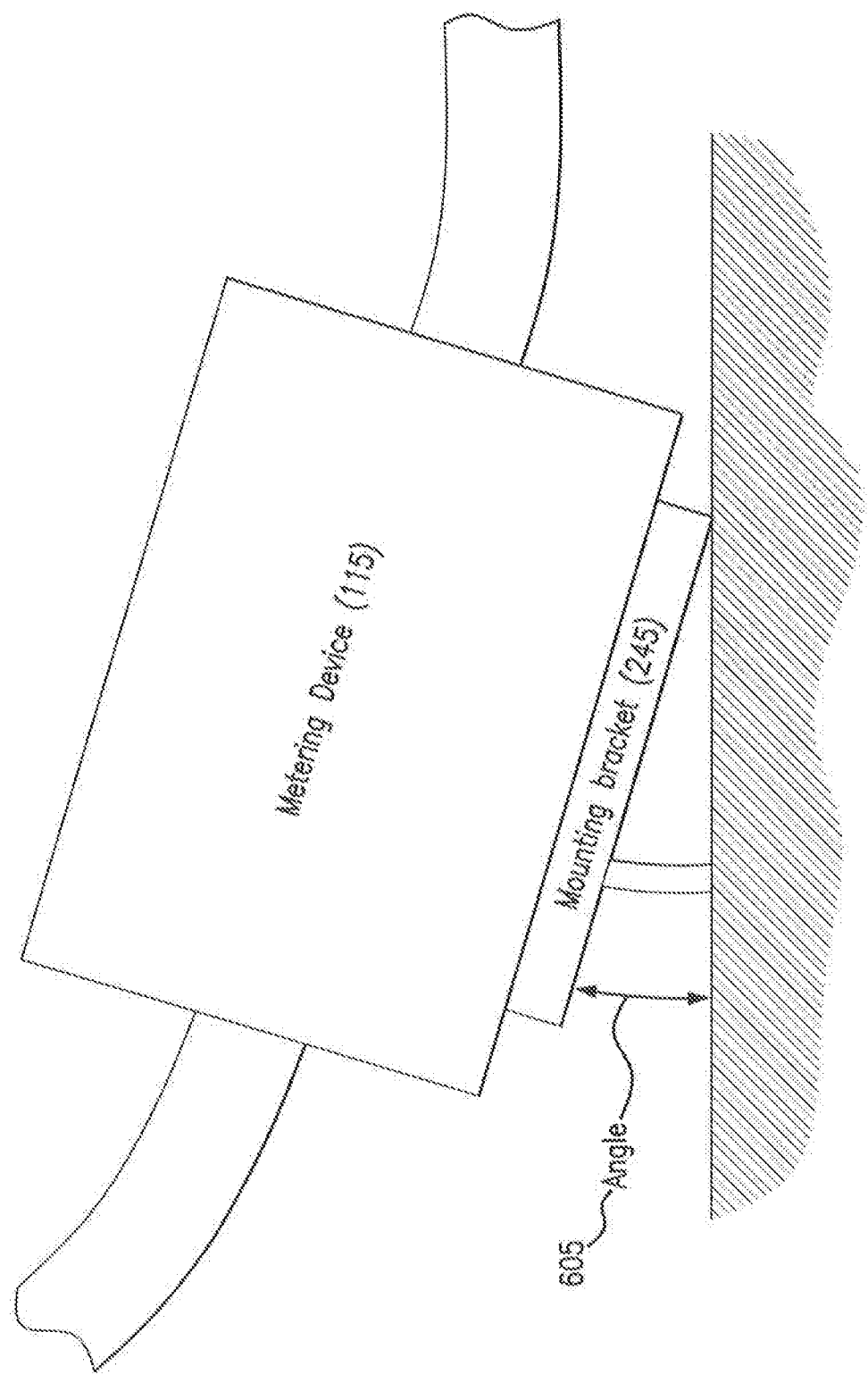
FIG. 6 illustrates the example metering device of the system of FIG. 1 positioned using a mounting bracket.

FIG. 6 illustrates the example metering device 115 of system 100 of FIG. 1 positioned using a mounting bracket 245. As shown in FIG. 6, metering device 115 includes a mounting bracket 245. Mounting bracket 245 may be used to adjust the position of metering device 115. For example, mounting bracket 245 may adjust an angle 605 at which metering device 115 rests. By adjusting this angle 605, the flow of fluid 208 through metering device 115 may be adjusted. In one embodiment, mounting bracket 245 may position metering device 115 at a substantially fifteen degree angle. This disclosure contemplates a position being substantially at a certain angle if it is within five degrees of that angle. This disclosure contemplates metering device 115 being positioned at any suitable angle.

As described above, metering device 115 may use particular components to control certain variables that affect the accuracy of the volume measurement made by metering device 115. For example, metering device 115 may use mounting bracket 245 to control an angle 605 of metering device 115 and heating elements 235 to control the temperature gradient between fluid 208 and metering device 115. However, this disclosure contemplates metering device 115 making volume measurements even without controlling for one or more of these variables by modifying lookup table 305 in certain embodiments.

In particular embodiments, metering device 115 may determine the cross-sectional area of fluid 208 at an electrode 215 without controlling the angle at which metering device 115 is positioned. Metering device 115 may include an accelerometer that measures the angle at which metering device 115 and/or tube 205 is positioned. The lookup table 305 may then be modified to include an additional column for the measured angle, resulting in a column for the conductance ratio $(G_R)$, a column for the cross-sectional area, and a column for the measured angle. The new lookup table may then include a first set of rows that show the correlation between $G_R$ and area at a first angle, a second set of rows that show the correlation between $G_R$ and area at a second angle, a third set of rows that show the correlation between $G_R$ and area at a third angle, and so on. Metering device 115 may determine the angle measured by the accelerometer and use that measured angle to index or interpolate into the corresponding set of rows in the new lookup table.

This new lookup table may be calibrated by repeating the previously described calibration process across various angles. Metering device 115 may then refer to this new lookup table to determine the area of electrodes in contact with fluid 208 based on a measured conductance ratio and an angle measured by the accelerometer. By including the angle in the lookup table, it may not be necessary to include mounting bracket 245 on metering device 115.

In certain embodiments, metering device 115 may determine the cross-sectional area of fluid 208 without controlling the temperature of electrodes 215 or the temperature gradient between electrodes 215 and fluid 208. Metering device 115 may include thermometers and/or temperature sensors that detect the temperature of electrodes 215 or fluid 208 and/or temperature gradient between electrodes 215 and fluid 208. The lookup table 305 may then be modified to include an additional column for the measured temperature or temperature gradient, resulting in a column for the conductance ratio ($G_R$), a column for the area, and a column for the measured temperature or temperature gradient. The new lookup table may then include a first set of rows that show the correlation between $G_R$ and area at a first temperature or temperature gradient, a second set of rows that show the correlation between $G_R$ and area at a second temperature or temperature gradient, a third set of rows that show the correlation between $G_R$ and area at a third temperature or temperature gradient, and so on. Metering device 115 may determine the temperature or temperature gradient measured by the temperature sensor and use that measured temperature or temperature gradient to index or interpolate into the corresponding set of rows in the new lookup table.

This new lookup table may be calibrated by repeating the previously described calibration process across various temperatures and temperature gradients. Metering device 115 may then refer to this new lookup table to determine the cross-sectional area of fluid 208 based on a measured conductance ratio and a temperature or temperature gradient measured by the temperature sensors. In certain embodiments, by including the temperature and/or temperature gradient in the lookup table, it may not be necessary to include heating elements 235 in metering device 115.

This disclosure contemplates the lookup table including any number of columns for any measured variables. The lookup table may include one or more columns for area, conductance ratio, temperature of fluid 208, temperature of electrodes 215, temperature gradient, and/or angle. For example, the lookup table may be a combination of the two previously described modified lookup tables such that the lookup table includes a column for a measured angle, a column for a measured temperature of electrodes 215, a column for $G_R$, and a column for area. Metering device 115 may then use a measured angle to index into a set of rows of the table corresponding to that measured angle. Metering device 115 may then use a measured temperature gradient to index into a subset of rows in the set of rows of the table corresponding to the measured angle and the measured temperature gradient. Metering device 115 may then interpolate using that subset of rows to determine the area for a measured $G_R$.

Figure 7:
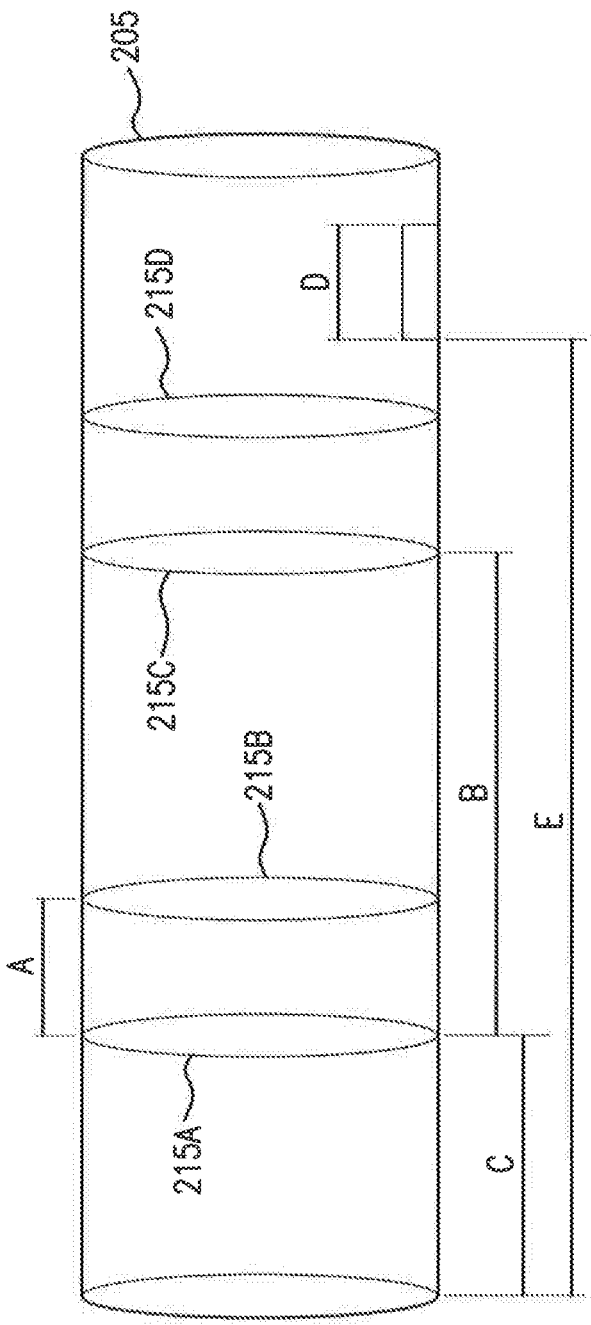
FIG. 7 illustrates example dimensions for the metering device of the system of FIG. 1.

FIG. 7 illustrates the example metering device 115 of system 100 of FIG. 1. The example metering device shown in FIG. 7 has specific dimensions and/or configurations to improve the accuracy of the metering device. Specifically, certain dimensional ratios have been selected to improve the accuracy of the metering device. These ratios are tied to the diameters of the electrodes 215.

The first ratio is the ratio of the diameter of the electrodes and the distance between the electrodes 215 of each electrode pair. This distance is labeled with the letter A. The ratio between the diameter of the electrode 215 and the distance A is substantially 1.372.

The second ratio is between the diameter of the electrodes 215 and the distance between the electrode pairs. This distance is labeled B. The ratio between the diameter of the electrodes and the distance B is substantially 0.4133.

The third ratio is between the diameter of the electrodes 215 and the distance between the first electrode 215A and an end of the tube 205. This distance is labeled C. The ratio between the diameter of the electrodes and the distance C is substantially 0.2533.

The fourth ratio is the ratio between the diameter of the electrodes and the length of the reference device. This length is labeled D. The ratio between the diameter of the electrodes and the length D is substantially 0.775.

The fifth ratio is between the diameter of the electrodes and the distance between an end of the tube 205 and the referenced device. This distance is labeled E. The ratio between the diameter of the electrodes and the distance E is substantially 0.1187.

The last ratio is between the diameter of the electrodes and the width of the electrodes, which is substantially 3.1. The width of the electrodes in certain embodiments is 0.25 inches. In the example of FIG. 7, the width of an electrode is the width of the material used to form the electrode. For example, if an electrode is formed by shaping a wire into an oval shape, as shown in FIG. 7, the width of the electrode is the width of the wire.

This disclosure contemplates a ratio being substantially a certain value if the ratio deviates from that value by less than or equal to 15% of that value.

Figure 8:
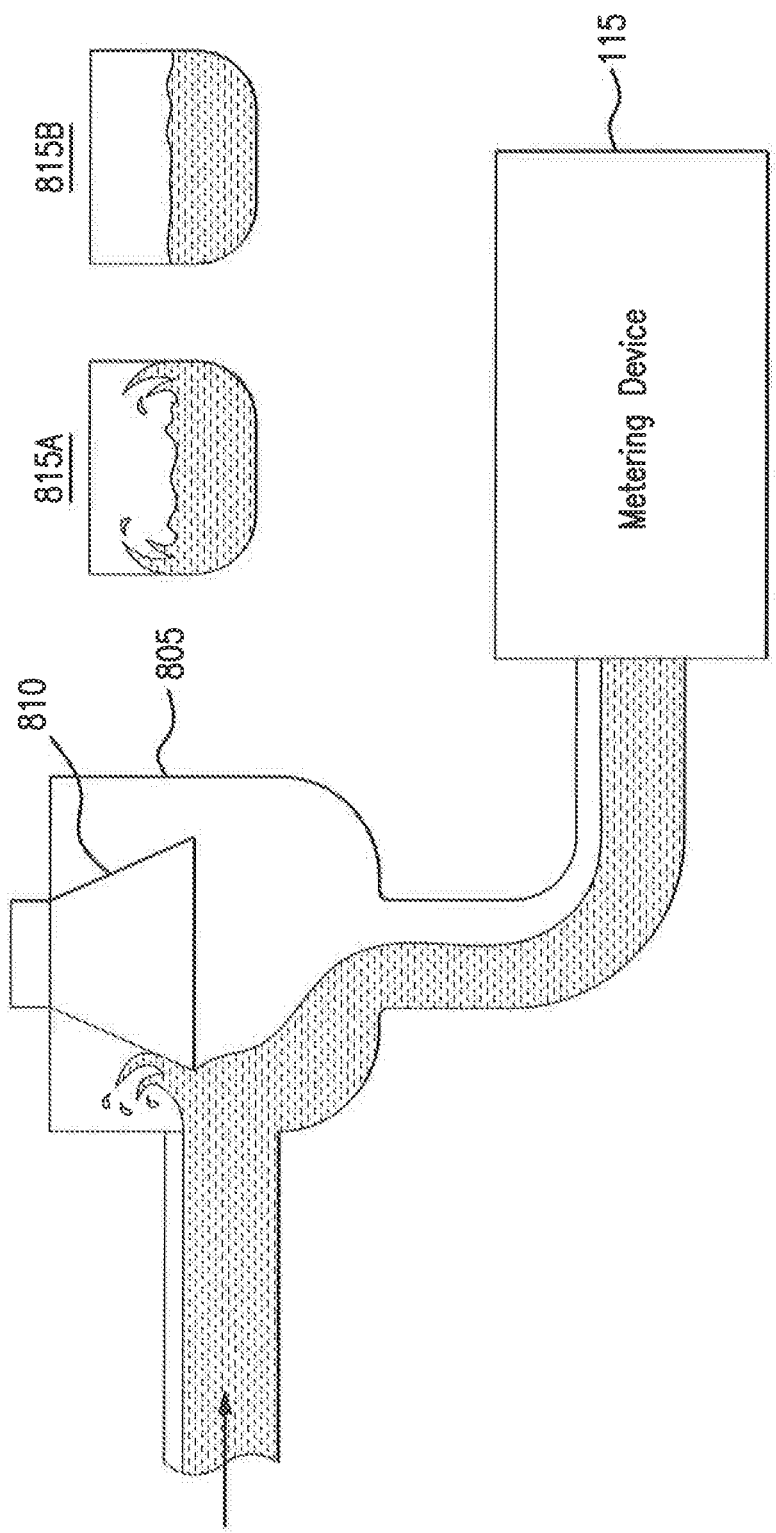
FIG. 8 illustrates the example metering device of the system of FIG. 1 used in conjunction with a stop valve.

FIG. 8 illustrates the example metering device 115 of system 100 of FIG. 1 used in conjunction with a stop valve 805. Fluids occasionally enter metering device 115 in a turbulent or spraying fashion. This may occur when the pressure of the fluid is too high. As a result of the turbulence and/or spraying, the accuracy of metering device 115 may be reduced. For example, excessive turbulence and/or spraying could cause the fluid to slosh and/or splash in the metering device 115, as depicted in cross-sectional view 815A. As the fluid sloshes in the metering device (e.g., against the sides of metering device 115 and/or the tube), the surface area of an electrode in contact with the fluid changes unpredictably and not as a function of the actual volume of the fluid in metering device 115. Furthermore, sloshing may create localized phenomena (e.g., whirlpools and backflows) that affect the speed of the fluid proximate the location of the phenomena. As a result, the speed of the fluid may become inconsistent through the length of metering device 115 and, as a result, throw off the volume measurements made by metering device 115.

In certain embodiments, a stop valve 805 may be used to reduce the turbulence and/or spray of the fluid as it enters metering device 115. As shown in FIG. 8, metering device 115 includes a tube in which a fluid flows. The tube is coupled to a stop valve 805. As the fluid flows towards metering device 115, it first enters stop valve 805. Stop valve 805 may include a triangular or trapezoidal component 810 that comes in contact with the fluid entering stop valve 805. That component may be made of plastic, rubber, metal, or any other suitable material. When the fluid comes in contact with that component 810, the fluid may splash against the component 810 and then flow downward through valve 805 in a less turbulent fashion. In other words, component 810 functions to absorb some of the momentum and turbulence of the fluid before the fluid enters metering device 115. As a result, the fluid may enter metering device 115 in a smooth and controlled fashion, as shown in cross-sectional view 815B, rather than in a turbulent or spraying fashion, as shown in cross-sectional view 815A.

Figure 9A:
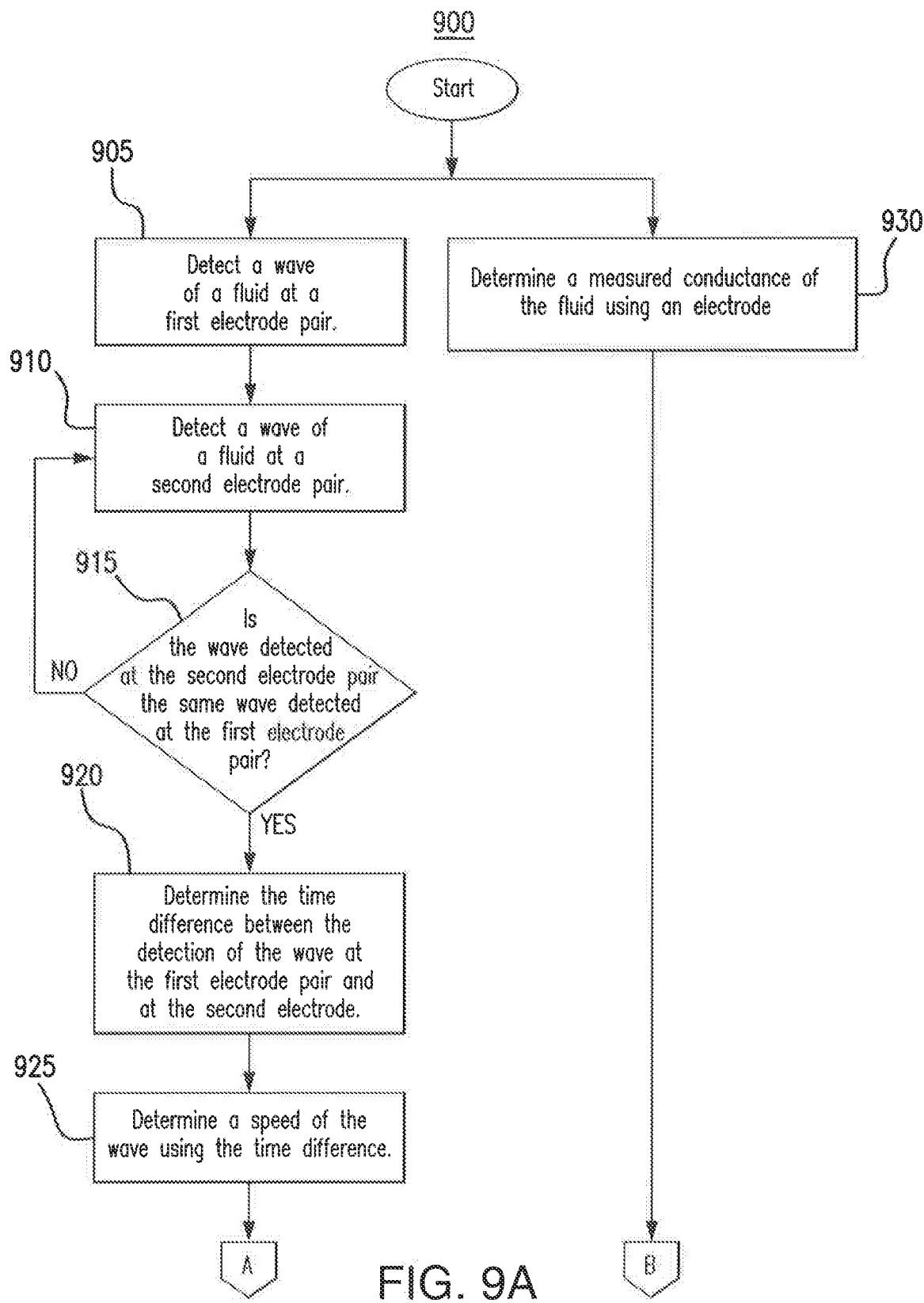
FIGS. 9A-9B show a flowchart illustrating a method for determining the volume of a fluid.
Figure 9B:
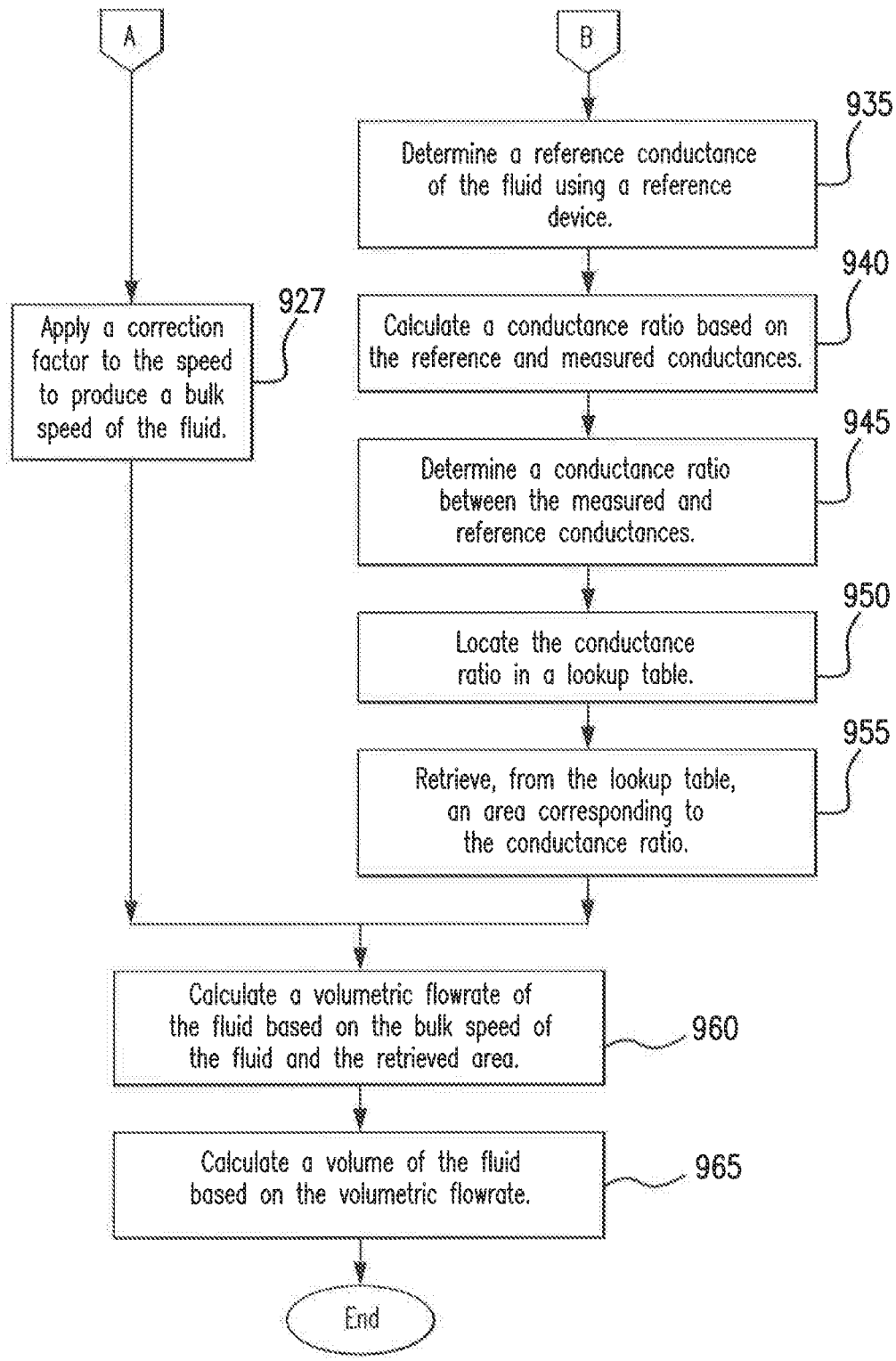

FIGS. 9A and 9B show a flowchart illustrating a method 900 for determining the volume of a fluid. In particular embodiments, metering device 115 performs method 900. As illustrated in FIGS. 9A and 9B, steps 905-927 can be performed in parallel with steps 930-955. However, this disclosure contemplates these steps being performed in series or in any suitable order.

Metering device 115 begins by detecting a wave of a fluid at a first electrode pair in step 905. In step 910, metering device 115 detects a wave of a fluid at a second electrode pair. Metering device 115 then determines whether the wave detected at the first electrode pair is the same wave detected at the second electrode pair. As discussed above, metering device 115 may make this determination by comparing amplitudes, frequencies, and adjacent waves of the detected waves. If the waves are not the same, metering device 115 returns to step 910 and monitors the second electrode pair for waves. If the detected waves are the same, metering device 115 determines a time difference between the detection of the wave at the first electrode pair and at the second electrode pair in step 920. This time difference represents the amount of time it took for the wave to travel between the first and second electrode pairs. In step 925, metering device 115 determines a wave speed using the time difference. As discussed previously, metering device 115 can determine the wave speed by dividing the distance between the first and second electrode pairs by the time difference. In step 927, metering device 115 applies a correction factor to the speed to produce a bulk speed of the fluid. As discussed above, the correction factor may be a function of the cross-sectional area of the fluid at an electrode.

Metering device 115 determines a measured conductance of the fluid using an electrode in step 930. The measured conductance may vary depending on the cross-sectional area of the fluid at an electrode. As discussed above, metering device 115 may measure the conductance by conducting an electric signal from a first electrode through the fluid to a second electrode. Metering device 115 may determine a change (e.g., a voltage drop) experienced by the electric signal as it traveled through the fluid. The fluid has a measurable conductance which causes the change to the electric signal.

Metering device 115 then determines a reference conductance of the fluid using a reference device in step 935. As discussed previously, the reference device may be fully submerged in the fluid so that it is fully in contact with the fluid. Metering device 115 may determine the reference conductance by conducting an electric signal from one portion of the reference device through the fluid to another portion of the reference device. Metering device 115 may determine a change (e.g., a voltage drop) experienced by the electric signal as it traveled through the fluid between the portions. The fluid has a measurable conductance which causes the change to the electric signal.

In step 940, metering device 115 calculates a conductance ratio based on the reference and measured conductances. In step 945, metering device 115 determines a conductance ratio between the measured and reference conductances. The ratio may be $G_R$ discussed previously. Metering device 115 locates the conductance ratio in a lookup table in step 950. The lookup table may include a plurality of entries. Each entry may indicate a conductance ratio and a corresponding cross-sectional area. In step 955, metering device 115 retrieves from the lookup table a cross-sectional area corresponding to the conductance ratio. The retrieved area may indicate a cross-sectional area of the fluid at an electrode.

In step 960, metering device 115 calculates a volumetric flowrate of the fluid based on the speed of the fluid and the cross-sectional area of the fluid. As discussed previously, the volumetric flowrate can be calculated by multiplying the speed of the fluid by the cross-sectional area. This step can be repeated across several intervals to determine the volumetric flowrate of the fluid as a function of time. In step 965, metering device 115 calculates a volume of the fluid based on the volumetric flowrate. As discussed previously, metering device 115 may determine the volume of the fluid by summing the determined volumetric flowrates multiplied by the time intervals and/or by integrating the volumetric flowrate across a period of time, for example, by using the rectangle approximation method of numeric integration.

Modifications, additions, or omissions may be made to the systems and apparatuses described herein without departing from the scope of the disclosure. The components of the systems and apparatuses may be integrated or separated. Moreover, the operations of the systems and apparatuses may be performed by more, fewer, or other components. Additionally, operations of the systems and apparatuses may be performed using any suitable logic comprising software, hardware, and/or other logic. As used in this document, "each" refers to each member of a set or each member of a subset of a set.

Modifications, additions, or omissions may be made to method 900 depicted in FIG. 9. Method 900 may include more, fewer, or other steps. For example, steps may be performed in parallel or in any suitable order. While discussed as metering device 115 (or components thereof) performing the steps, any suitable component of system 100 may perform one or more steps of the method.

Although the present disclosure includes several embodiments, a myriad of changes, variations, alterations, transformations, and modifications may be suggested to one skilled in the art, and it is intended that the present disclosure encompass such changes, variations, alterations, transformations, and modifications as fall within the scope of the appended claims.

What is claimed is:

1. An apparatus comprising:
   a tube;
   a first pair of electrodes coupled to the tube, the first pair of electrodes comprising a first electrode and a second electrode;
   a second pair of electrodes coupled to the tube, the second pair of electrodes comprising a third electrode and a fourth electrode;
   a reference device coupled to the tube; and
   a processor configured to:
      determine a speed of a fluid traveling between the first pair of electrodes and the second pair of electrodes;
      determine a reference conductance of the fluid using the reference device;
      determine a measured conductance of the fluid using at least one of the first pair of electrodes and the second pair of electrodes;
      determine a conductance ratio between the measured conductance and the reference conductance;
      locate the conductance ratio in a lookup table;
      retrieve, from the lookup table, an area corresponding to the conductance ratio, wherein the retrieved area indicates a cross-sectional area of the fluid at one or more of the first, second, third, and fourth electrodes;

add a correction factor to the speed to produce a bulk speed of the fluid;

determine a volumetric flow rate of the fluid based on the bulk speed and the retrieved area; and determine a volume of the fluid based on the determined volumetric flow rate.

2. The apparatus of claim 1, further comprising a heating element coupled to at least one of the first electrode, the second electrode, the third electrode, the fourth electrode, and the reference device, the heating element configured to heat at least one of the first electrode, the second electrode, the third electrode, the fourth electrode, and the reference device to substantially 85 degrees Fahrenheit.

3. The apparatus of claim 1, further comprising a temperature sensor configured to measure a temperature of the fluid, wherein the processor is further configured to determine the area further based on the measured temperature.

4. The apparatus of claim 1, further comprising a mounting bracket coupled to the tube, the mounting bracket configured to position the tube at a substantially fifteen degree angle.

5. The apparatus of claim 1, further comprising an accelerometer configured to measure an angle at which the tube is positioned, wherein the processor is further configured to determine the area further based on the measured angle.

6. The apparatus of claim 1, wherein:
a ratio between a diameter of the first electrode and a width of the first electrode is substantially 3.1;
a ratio between a diameter of the first electrode and a distance between the first electrode and the second electrode is substantially 1.372;
a ratio between the diameter of the first electrode and a distance between the first electrode and the third electrode is substantially 0.4133;
a ratio between the diameter of the first electrode and a distance between the first electrode and an end of the tube is substantially 0.2533;
a ratio between the diameter of the first electrode and a length of the reference device is substantially 0.775; and
a ratio between a diameter of the fourth electrode and a distance between the end of the tube and the reference device is substantially 0.1187.

7. The apparatus of claim 1, further comprising a stop valve coupled to the tube.

8. The apparatus of claim 1, wherein the first pair of electrodes, the second pair of electrodes, and the reference device are coupled to a ground different from earth ground.

9. The apparatus of claim 1, further comprising a capacitor coupled to at least one of the first electrode, the second electrode, the third electrode, and the fourth electrode, the capacitor configured to remove a direct current component from a measuring signal communicated through at least one of the first electrode, the second electrode, the third electrode, and the fourth electrode.

10. The apparatus of claim 1, further comprising a switching regulator coupled to the processor.

11. The apparatus of claim 1, wherein the lookup table comprises a plurality of entries, each entry of the plurality of entries indicating a conductance ratio and a corresponding area.

12. A method comprising:
determining a speed of a fluid traveling through a tube between a first pair of electrodes and a second pair of electrodes coupled to the tube, the first pair of electrodes comprising a first electrode and a second electrode, the second pair of electrodes comprising a third electrode and a fourth electrode;

determining a reference conductance of the fluid using a reference device coupled to the tube;

determining a measured conductance of the fluid using at least one of the first pair of electrodes and the second pair of electrodes;

determining a conductance ratio between the measured conductance and the reference conductance;

locating the conductance ratio in a lookup table;

retrieving, from the lookup table, an area corresponding to the conductance ratio, wherein the retrieved area indicates a cross-sectional area of the fluid at one or more of the first, second, third, and fourth electrodes;

adding a correction factor to the speed to produce a bulk speed of the fluid;

determining a volumetric flow rate of the fluid based on the bulk speed and the retrieved area; and determining a volume of the fluid based on the determined volumetric flow rate.

13. The method of claim 12, further comprising heating at least one of the first electrode, the second electrode, the third electrode, the fourth electrode, and the reference device to substantially 85 degrees Fahrenheit.

14. The method of claim 12, further comprising measuring a temperature of the fluid, wherein determining the area is further based on the measured temperature.

15. The method of claim 12, further comprising positioning the tube at a substantially fifteen degree angle using a mounting bracket.

16. The method of claim 12, further comprising measuring an angle at which the tube is positioned, wherein determining the area is further based on the measured angle.

17. The method of claim 12, wherein:
a ratio between a diameter of the first electrode and a width of the first electrode is substantially 3.1;
a ratio between a diameter of the first electrode and a distance between the first electrode and the second electrode is substantially 1.372;
a ratio between the diameter of the first electrode and a distance between the first electrode and the third electrode is substantially 0.4133;
a ratio between the diameter of the first electrode and a distance between the first electrode and an end of the tube is substantially 0.2533;
a ratio between the diameter of the first electrode and a length of the reference device is substantially 0.775; and
a ratio between a diameter of the fourth electrode and a distance between the end of the tube and the reference device is substantially 0.1187.

18. The method of claim 12, wherein the first pair of electrodes, the second pair of electrodes, and the reference device are coupled to a ground different from earth ground.

19. The method of claim 12, further comprising removing a direct current component from a measuring signal communicated through at least one of the first electrode, the second electrode, the third electrode, and the fourth electrode.

20. The method of claim 12, wherein the lookup table comprises a plurality of entries, each entry of the plurality of entries indicating a conductance ratio and a corresponding area.

* * * * *